United States Patent
Carpentier

(10) Patent No.: US 8,597,338 B2
(45) Date of Patent: Dec. 3, 2013

(54) INTRACEREBRAL PROBE AND DEVICE FOR THE TREATMENT OF NEUROLOGICAL OR PSYCHIATRIC DYSFUNCTIONS

(75) Inventor: Alexandre Carpentier, Paris (FR)

(73) Assignee: Assistance Publique Hopitaux de Paris, Paris (FR)

( * ) Notice: Subject to any disclaimer, the term of this patent is extended or adjusted under 35 U.S.C. 154(b) by 786 days.

(21) Appl. No.: 12/063,837

(22) PCT Filed: Aug. 18, 2006

(86) PCT No.: PCT/FR2006/050806
§ 371 (c)(1),
(2), (4) Date: Mar. 9, 2010

(87) PCT Pub. No.: WO2007/020363
PCT Pub. Date: Feb. 22, 2007

(65) Prior Publication Data
US 2010/0168826 A1    Jul. 1, 2010

(30) Foreign Application Priority Data
Aug. 18, 2005    (FR) ..................................... 05 08595

(51) Int. Cl.
*A61H 21/00* (2006.01)
*A61B 5/04* (2006.01)
*A61B 18/18* (2006.01)

(52) U.S. Cl.
USPC ............. 607/89; 600/372; 600/373; 600/544; 606/2; 606/14

(58) Field of Classification Search
USPC .......................... 606/2–26; 600/372–378, 544
See application file for complete search history.

(56) References Cited

U.S. PATENT DOCUMENTS

| | | | |
|---|---|---|---|
| 5,785,704 A | 7/1998 | Bille et | |
| 5,995,868 A | 11/1999 | Dorfmeister et al. | |
| 6,109,270 A | 8/2000 | Mah et al. | |
| 6,129,685 A | 10/2000 | Howard, III | |
| 6,375,666 B1 | 4/2002 | Mische | |
| 6,629,973 B1 | 10/2003 | Wardell et al. | |
| 6,629,990 B2 | 10/2003 | Putz et al. | |
| 6,718,196 B1 * | 4/2004 | Mah et al. ...................... | 600/476 |
| 2002/0077643 A1 * | 6/2002 | Rabiner et al. ................ | 606/169 |
| 2003/0009207 A1 | 1/2003 | Paspa et al. | |
| 2003/0088189 A1 * | 5/2003 | Tu et al. ........................ | 600/549 |
| 2004/0215162 A1 | 10/2004 | Putz | |
| 2007/0010860 A1 * | 1/2007 | Gafni et al. .................... | 607/96 |

FOREIGN PATENT DOCUMENTS

DE          101 46 762          5/2003

* cited by examiner

*Primary Examiner* — Dawayne A Pinkney
(74) *Attorney, Agent, or Firm* — Leffert Jay & Polglaze, P.A.

(57) ABSTRACT

An intracerebral probe (11) comprising a first part (20) with laser or cryogenic treatment means and further comprising a hollow second part (22) surrounding the first, the first part sliding inside the second part along its longitudinal axis (A); and a plurality of detectors (16) distributed along a portion of the second part (22) in such a manner as to be capable of identifying a brain dysfunction zone along the longitudinal axis (A) of the second part. Advantageously, the probe presents a lateral treatment window enabling the action of the treatment means to be directed. The invention also provides a kit and a treatment system including such a probe, and the use thereof of treating cell dysfunctions that give rise to neurological or psychiatric symptoms.

21 Claims, 3 Drawing Sheets

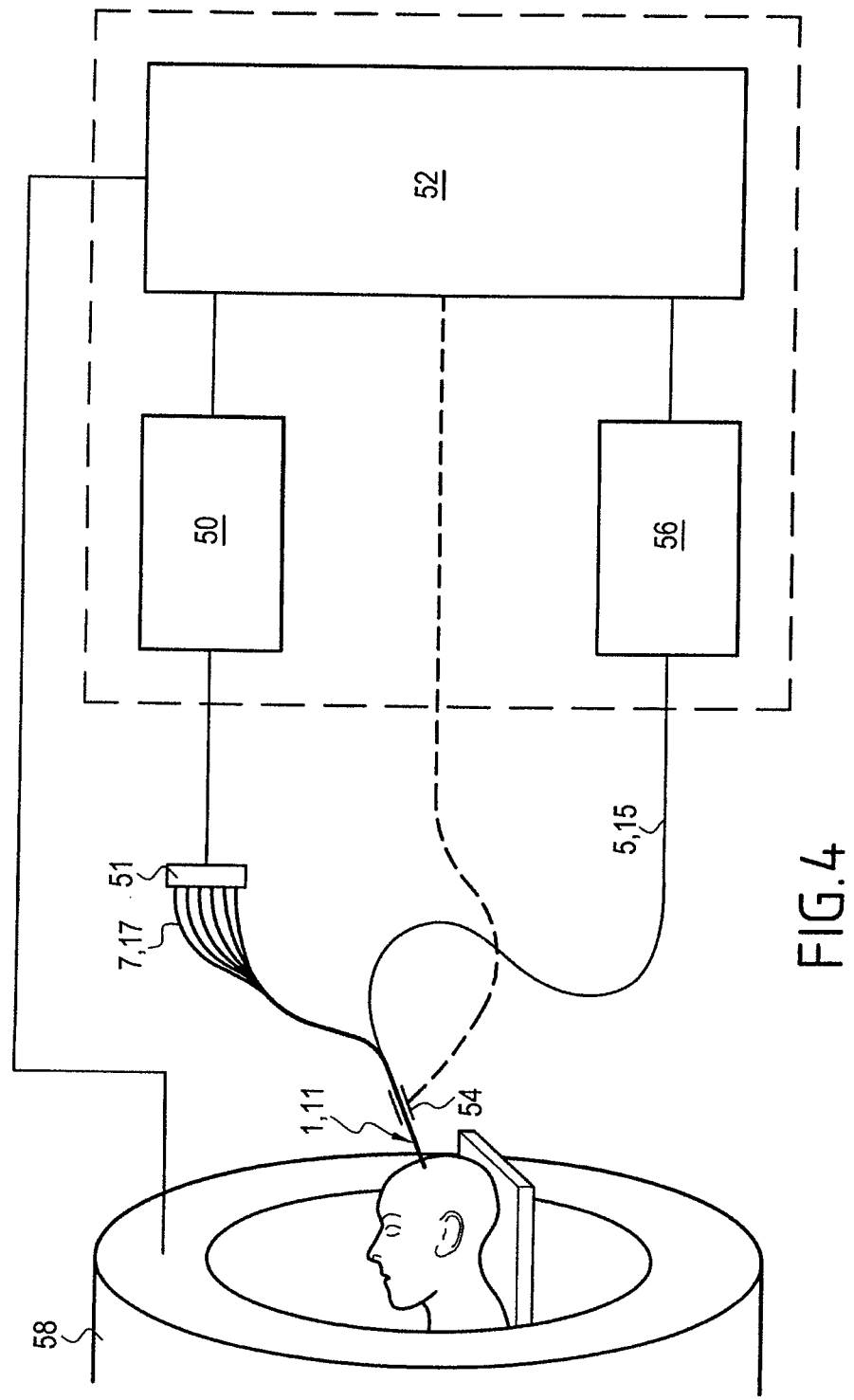

INTRACEREBRAL PROBE AND DEVICE FOR THE TREATMENT OF NEUROLOGICAL OR PSYCHIATRIC DYSFUNCTIONS

The invention relates to an intracerebral probe that is implantable in a human or animal brain, and to a treatment system including such a probe, for treating zones of the brain that are subject to dysfunctions.

Such a probe is implanted temporarily in the brain to apply treatment locally to a brain dysfunction zone. It is used in particular for treating metabolic or electrophysiological dysfunctions of the brain that give rise to neurological or psychiatric symptoms or diseases, such as, for example: epilepsy, Parkinson's disease, compulsive obsessional disorders, depression, etc.

Several types of intracerebral probe already exist, each type using different treatment means, and in particular: the use of mechanical stresses as in U.S. Pat. No. 6,375,666; heating by means of a so-called radiofrequency heater resistance; cooling by means of devices such as a Peltier cooler or a thermoelectric cooler, as in U.S. Pat. No. 6,629,990; electrical stimulation; chemical treatment by means of a therapeutic liquid (generally a cytotoxic agent or an apoptosis inducing agent), as in US 2004/0215162; a laser; and cryogenic means.

The invention relates only to the two last-mentioned types of treatment means, i.e. laser and cryogenic means; Compared with the other treatment means, laser and cryogenic means present the following advantages in particular:

It is possible to perform so-called morphological tracking by using magnetic resonance imaging (MRI) because probes for laser or cryogenic treatment are compatible with MRI. The intensity and the dissipation of heat (with a laser) or of cold (with cryogenic means) inside the brain can thus be viewed during treatment so as to be able to stop the treatment or reduce its intensity, where necessary.

It is possible to perform so-called "electrophysiological" tracking by continuous electrical recording, where that is not possible with thermoelectrical treatment means since they disturb the recording made.

Probes for laser or cryogenic treatment are well known and they are used as follows.

Firstly, the positions of the dysfunction zones that are to be destroyed are identified. Coarse initial identification of position can be performed by magnetic resonance imaging (MRI).

Thereafter, finer position identification is performed by using a so-called "detector" probe carrying a plurality of detectors on its intracerebral portion that are suitable for detecting dysfunction in the brain zones surrounding it. US 2003/0009207 describes a detection probe with a plurality of electrodes distributed over its intracerebral portion. Each electrode serves to pick up signals of the electroencephalogram (EEG) type that are representative of the electrical activity of the brain zones surrounding the electrode. On the basis of such a signal it is possible to identify brain dysfunction in the vicinity of one of the electrodes. For example, document U.S. Pat. No. 5,995,868 describes an EEG analysis method that makes it possible to identify a dysfunction that is a precursor to an epileptic attack.

Finally, the detection intracerebral probe is withdrawn and a laser or cryogenic treatment probe is inserted in its place.

In spite of being effective in certain specific situations, existing intracerebral probes present numerous drawbacks:

Laser or cryogenic treatment probes perform a therapeutic function only and they do not perform a diagnostic function. It is therefore necessary to insert and then withdraw a detection probe, prior to inserting the laser or cryogenic treatment probe in its place.

Probes that enable a therapeutic liquid or other chemical treatment to be injected as in US 2004/0215162 have a therapeutic effect that is spherical around the point where said liquid is injected (generally situated at the distal end of the probe), which does not make it possible to take account of the complex anatomy of the brain zones for treatment. This therefore gives rise to treatment that is anatomically incomplete or excessive.

An object of the invention is to provide an intracerebral probe making it possible firstly to detect dysfunctional zones and secondly to apply laser or cryogenic treatment to said zones, i.e. a probe that is designed simultaneously to perform a diagnostic action, a therapeutic action, and an action of monitoring the effectiveness of the treatment.

For this purpose, the invention provides an intracerebral probe comprising a first part (or inner part) with laser or cryogenic treatment means, the probe further comprising: a hollow second part (or outer part) surrounding the first, the first part sliding inside the second part along its longitudinal axis; and a plurality of detectors distributed along a portion of the second part in such a manner as to be capable of identifying a brain dysfunction zone along the longitudinal axis of the second part (reference is made below to axial position identification).

With such a probe, the second part of the probe is implanted first. The first part is implanted either together with the second part, or else by being caused to slide inside the second part that has already been implanted. There is thus no need to withdraw the second part in order to implant the first. This makes it possible to avoid "go-and-return" phenomena when using different probes in the brain. Furthermore, the second part serves to guide the first part so that the positioning of the laser or cryogenic treatment means is improved.

In an embodiment, the detectors are electrodes, each electrode being capable of detecting electrical activity in the surrounding zone of the brain. Electrical activity of the brain is a good indicator of neurological dysfunction. In addition, the electrodes enable positions to be identified precisely along the longitudinal axis of the second part. Finally, these electrodes serve to perform electrophysiological tracking while treatment is taking place by making a continuous electrical recording from the zone being treated.

In an embodiment, the detectors (e.g. the electrodes) are distributed circumferentially over the second part, around its longitudinal axis, or are segmented circumferentially so as to be capable of identifying the position of a brain dysfunction zone angularly around said longitudinal axis. For example, the second part may carry (at a determined axial position) four detectors or an annular detector segmented into four segments, these detectors or these segments being distributed angularly at 0°, 90°, 180°, and 270° around the probe. This makes it possible to perform angular position identification, in addition to the above-mentioned axial position identification.

Once the axial and angular position of the dysfunctional zone has been identified, it is advantageous to be able to direct the action of the treatment means onto the identified zone in order to treat only that zone. A drawback of laser or cryogenic treatment means is that by default they act over 360° around the source of laser or cold emission (situated on the first probe part).

That is why, in an embodiment of the invention, the second part of the probe presents at least one lateral treatment window making it possible to direct the action of the treatment means, i.e. to direct the emission of laser radiation or of cold along a certain direction.

The zone of laser or cryogenic emission from the treatment means is thus determined by the position, the shape, and the size of said window.

If the treatment window extends over less than 360° around the second part of the probe, then the action of the treatment means can be directed angularly. For example, if the treatment window occupies 180°, it becomes possible to treat a zone of the brain that is situated on one side of the probe, without treating the zone situated on the opposite side.

In an embodiment, the probe comprises laser treatment means, said lateral treatment window being a window that is transparent to the laser radiation emitted by said treatment means.

Advantageously, said lateral treatment window extends along the longitudinal axis of the second part and/or circumferentially around said axis. By causing the first part of the probe to slide in the second part along the longitudinal axis of the second part, it is possible to move the laser treatment means inside the window. For a given position of the second part of the probe, it is thus possible to treat a brain zone of large axial and/or circumferential extent. In addition, since the first part of the probe is not in contact with brain tissue, moving it does not damage any of this tissue.

In an embodiment, the circumferential width of said lateral treatment window varies along the longitudinal axis of the second part. For example, the treatment window may be T-shaped (or +-shaped) with one limb of the T-shape (or of the +-shape) extending circumferentially and the other limb of the T-shape (or +-shape) extending axially. In another example, the treatment window may be V-shaped. Such T-, +-, or V-shapes can also be obtained by juxtaposing a plurality of small windows. Thus, by moving the treatment means (i.e. the first part of the probe) along the longitudinal axis of the second part, the angular extent of the emission zone from the treatment means can be varied.

Naturally, the probe is implanted in a portion of the brain in which a dysfunction is liable to occur. This portion of the brain is "gridded", or rather subdivided into a plurality of detection zones defined by the detectors. Since the detectors are distributed along the longitudinal axis of the second part, or possibly circumferentially around said axis, the detection zones follow one another along said axis, or possibly around it.

It is then possible to leave the probe with its detectors in a fixed position for several hours or days while waiting to collect sufficient data. This embodiment also presents an advantage in detecting dysfunctions that occur only occasionally in time, such as those that give rise to attacks of epilepsy. Possibly, if no attack occurs naturally, an attack can be provoked by stimulating the corresponding portion of the brain, e.g. by causing an electric current to pass between two electrodes. These may either be additional electrodes fastened to the intracerebral portion of the second part of the probe and especially dedicated to stimulation, or else existing electrodes normally used as detectors, that are made to operate differently.

For other applications, such as continuous neurological disorders (e.g. Parkinson's disease), and psychiatric disorders, the detectors of said probe serve to detect electrophysiological, magnetic, or metabolic changes in the tissue (change in basic electrical activity, a change in spectrum, etc.), compared with known normal activity in a healthy subject for the zone in which detection is being performed.

The detectors used may be of various types and can thus be capable of detecting various parameters such as electrical activity, magnetic activity, and/or the local metabolism of brain tissues surrounding them. Advantageously, such detectors are distributed in the vicinity of the intracranial end of the second part of the probe. When the detectors are electrodes, the electrical activity detected by means of the electrodes may correspond to a potential difference between two of the electrodes (referred to as bipolar recording) or to the potential difference between one of the electrodes and an extracranial reference electrode (referred to as monopolar recording).

The invention also provides a kit comprising a probe of the invention, a guide for guiding the second part of the probe while it is being implanted in the brain, and a fastener system for holding said second part and the guide fixed in a determined relative position.

In an embodiment, the kit comprises a plastics sheath extending between said guide and the extracranial end of the first part of the probe so as to maintain a sterile environment for the junctions between the guide and the second part of the probe, and between the first and second parts of the probe.

The invention also provides a treatment system comprising a probe of the invention and control means for controlling the operation of said laser or cryogenic treatment means, said control means being connected to the detectors of the probe so as to be capable, during treatment, of receiving information from said detectors and of modulating the operation of said treatment means as a function of the information received.

This is another important aspect of the invention consisting in monitoring treatment in real time on the basis of information detected by the detectors situated in the vicinity of the zone being treated. When the detectors no longer detect the original dysfunction, this makes it possible to stop the treatment (or to reduce its intensity). Conversely, when the detectors do not detect disappearance of the original dysfunction, this makes it possible to increase the intensity of the treatment.

Advantageously, the treatment system further comprises a connection system for connecting said control means to an MRI appliance so as to be capable, during treatment, of receiving information from said MRI appliance and of modulating the operation of said treatment means as a function of the information received. This makes it possible in particular to monitor dissipation of heat/cold inside the brain during treatment. In the event of excessive heating/cooling that might constitute a danger for the brain, said control means stop the treatment or reduce its intensity. MRI tracking also makes it possible to verify whether the treatment is or is not effective, and to modulate the treatment accordingly.

The invention and its advantages can be better understood on reading the following detailed description. The description refers to the accompanying figures, in which:

FIG. 4 shows an example of a system of the invention.

Figure 1:
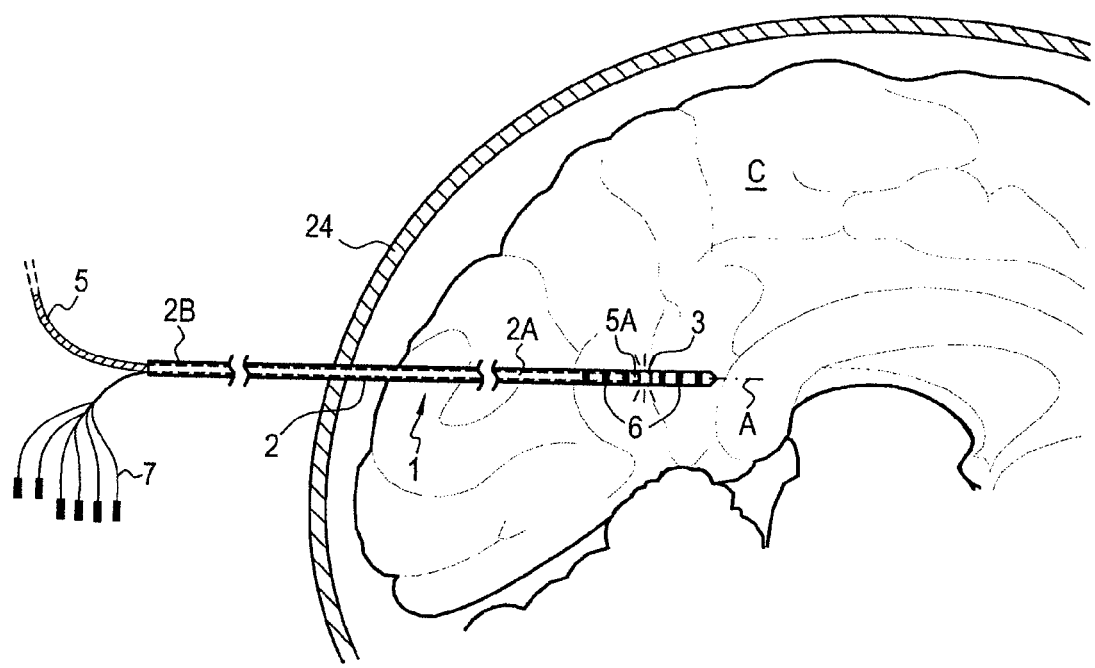
FIG. 1 shows a first example of a probe of the invention.

There follows a description of a first example of an intracerebral probe of the invention, given with reference to FIG. 1.

In this first embodiment, the probe comprises an inner part 5 having laser treatment means, and a hollow outer part 2 surrounding the inner part 5. The inner part 5 is mounted to slide inside the outer part 2 along its longitudinal axis. A plurality of detectors 6 are distributed along a portion of the outer part 2, situated close to its intracranial end 5A.

The probe 1 is long and thin and extends along its main axis A, which is also the longitudinal axis of the outer part 2 of the probe. The outer part 2 of the probe presents an intracerebral portion 2A that is inserted into the brain C, and an extracerebral portion 2B.

If the outer part 2 on its own does not present sufficient stiffness to be capable of being pushed into the brain without deforming, then means are used for stiffening it (not shown). By way of example, these means could be a tubular guide slid over the outside of the probe to increase its stiffness.

The outer part 2 presents, in front of the portion 2A, a treatment window 3 that is transparent to the laser radiation of the treatment means. Laser radiation can thus be emitted by the treatment window 3. This laser radiation is taken to the window 3 with the help of an optical fiber 5 that runs along the inner part 5 of the probe 1 as far as the intracranial end 5A of the part 5. Laser radiation can thus be emitted from said end 5A and can pass through the window 3 to reach the brain zone for treatment. The emitted laser radiation serves to destroy the tissue of the brain zone that is close to the radiation, by heating it.

Advantageously, a cooling system, e.g. a system for moving cooling liquid back and forth (not shown) is provided in the inner portion 5 of the probe in order to control (limit) heating of the brain C.

In general, in order to preserve healthy brain tissue, it is preferable to be able to control heating and monitor heat dissipation (or cold dissipation with cryogenic treatment) in various regions of the brain. By selecting a probe that is compatible with MRI, i.e. an "MRI compatible" probe, i.e. a probe that is not ferromagnetic, monitoring can be performed by MRI diffusion sequences while treatment is taking place.

The detectors 6 are distributed along the intracerebral portion 2A of the outer part 2, at the front thereof. These detectors 6 are distributed on either side of the treatment window 3 and they are connected to a measurement device, external the probe, by means of connections such as electric wires 7 that pass inside the outer part 2. These wires 7 are preferably not ferromagnetic. The detectors 6 are electrodes, e.g. made of titanium, platinum, or carbon.

Figure 2:
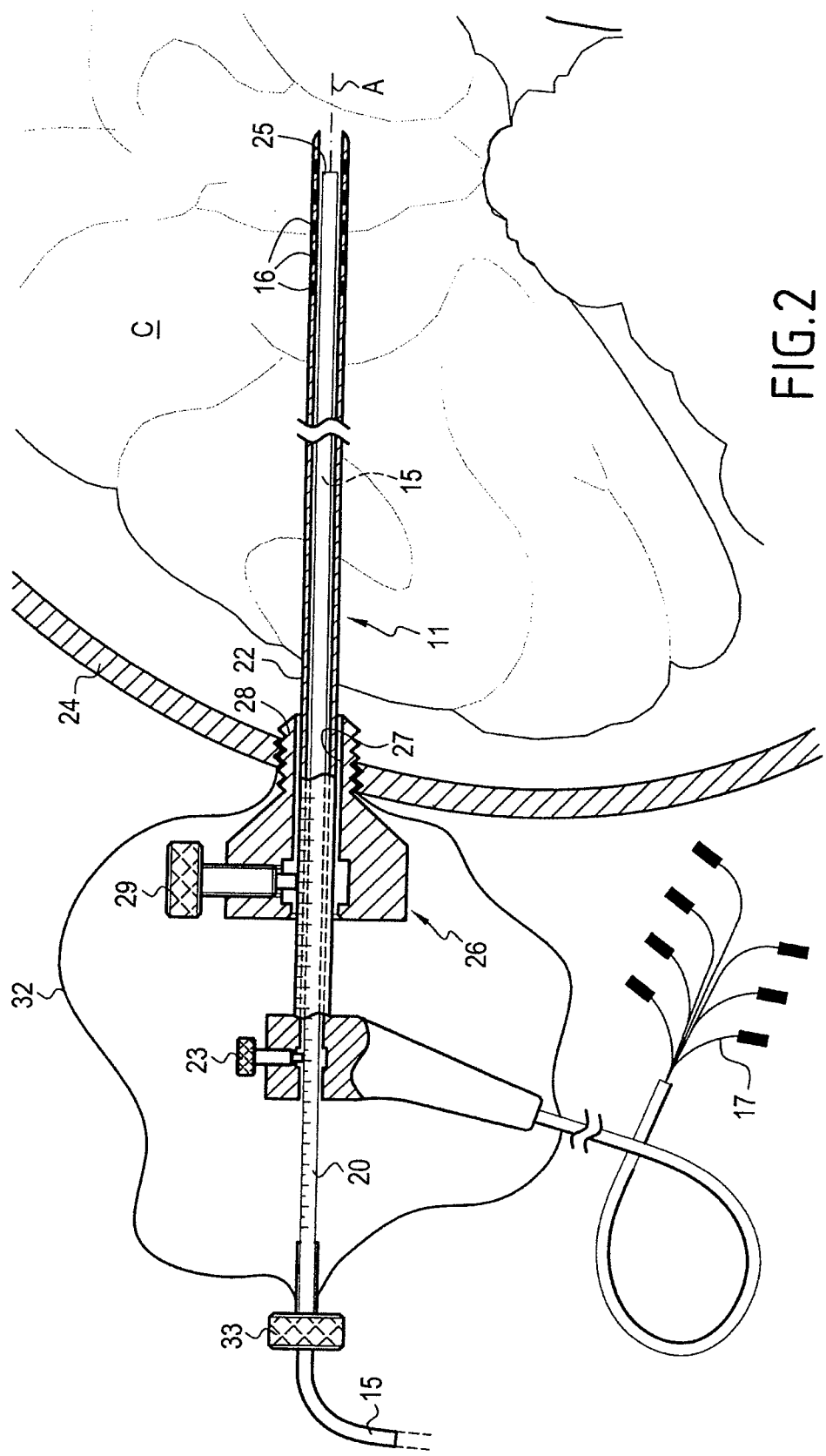
FIG. 2 is a section view of a second example of a probe of the invention.

There follows a description of a second embodiment of a probe of the invention, with FIG. 2 constituting an example thereof.

This embodiment comprises a probe 11 having an inner part 20 including means for laser or cryogenic treatment. The outer part 22 of the probe is placed around the inner part 20. The inner part 20 can slide inside the outer part 22 along the longitudinal axis A thereof.

In an embodiment, the inner part 20 is constituted by a glass fiber 15. Where necessary, fiber 15 is surrounded by a protective sheath. Laser radiation can be conveyed by the glass fiber 15 and can be emitted from the end 25 of the inner part.

In another embodiment, the inner part 20 is a cryogenic probe. In a well-known example of a cryogenic probe, the probe comprises three long tubes that are concentric (an inner tube, an intermediate tube, and an outer tube). The inner tube is used as a duct for conveying liquid nitrogen. The space between the inner tube and the intermediate tube is used as a duct for conveying nitrogen after it has passed into the gaseous state in a chamber situated at the intracranial end 25 of the inner part 20. The space between the intermediate tube and the outer tube constitutes an insulation space enabling the liquid nitrogen to reach said chamber without picking up heat. Such a cryogenic tube serves to freeze the tissue around said chamber, i.e. around the intracranial end 25. Naturally, other types of cryogenic probe could be used.

In order to make it easier to move the inner part 20 by hand, the inner part presents grip means 33. In this example, the grip means comprise a knurled wheel fastened to the extracranial end of the part 20.

The probe 11 also includes a fastener system mounted on one or the other of the parts of the probe and enabling the first and second parts of the probe to be fastened in a determined relative position. In this example, the outer part 22 may be held in a fixed position relative to the inner part 20 with the help of fastener means comprising a clamping screw 23, said means being fastened to the rear of the outer part 22 and being suitable for clamping onto the inner part 20 inside the outer part 22.

Advantageously, the inner part 20 is graduated in its clamping zone, thus making it possible to determine the relative position of the inner and outer parts 20 and 22 and/or to adjust this position manually with reference to the graduations.

The outer part 22 carries detectors 16. These detectors 16 are electrodes distributed along a portion of the outer part 22 in the vicinity of its intracranial end. These detectors 16 are connected to a measurement device, external to the probe, via connections, such as electric wires 17 passing along the outer part 22.

In order to implant the probe 11 in the brain C, a hole is trepanned through the patient's skull 24 and a guide 26 is used for guiding the part 22 of the probe while it is being implanted. A fastener system is also used for fastening this outer part 22 relative to the guide 26 in a determined relative position. In the example shown, the guide 26 has an opening 27 passing therethrough suitable for receiving the outer part 22 and having, at its front end, a threaded portion 28 suitable for being screwed into the skull 24, and at its rear end, a fastener system that comprises a clamping screw 29 that, when tightened, clamps the outer part 22 in the guide 26 so as to fasten the probe and the guide together in a determined relative position. Advantageously, graduations are present on the outer part 22 in the clamping zone so as to enable the position of the part 22 relative to the guide 26 to be identified visually and/or adjusted manually.

Such a probe 11 is used as follows: firstly the outer part 22 of the probe 11 is slid through the guide 26 and pushed into the patient's brain until it reaches the desired position. The outer part 22 can be pushed in on its own or together with the inner part 20. If the part 22 on its own or with the part 20 does not present sufficient thickness for it to be possible to push the probe in, then a mandrel is used that is slid inside the probe in order to make it stiffer.

It should be observed that the outer part 22 is open at both ends (and it is hollow from one end to the other). During implantation, it is appropriate to make sure that the inner part 20 or the mandrel, if any, closes the opening at the intracranial end of the outer part 22 so as to prevent material from penetrating through the opening.

Once the probe is in place, the electrical activity of the surrounding brain medium is detected using the detectors 16. If a neurological dysfunction occurs, the brain zone in which this dysfunction occurs is identified. Thereafter, the end 25 of the inner part 20 is moved up to said zone. (If the inner part 20 has not yet been inserted into the outer part 22, this is the moment is it inserted.) Once the end 25 is in the proper location, the outer part 22 is pulled back so as to uncover (strip) the end 25 so that the laser or cryogenic treatment can reach the dysfunctional zone and treat it. The treatment stage is generally started only once the end 25 has been uncovered.

In this embodiment, the outer part 22 thus forms a protective sheath around the laser or cryogenic treatment means until they are striped by withdrawing said outer part 22. Once the treatment has been performed, it is possible to cover up the treatment means by pushing in said outer part 22. Such a configuration makes it possible to have a maximum number of detectors on the outer part 22.

During operation, a sterile protective pouch 32 of plastics material is secured firstly around the guide 26 and secondly around the extracranial end of the inner part 20, in front of the knurled wheel 33, so that the wheel 33 is outside the pouch 32. The pouch 32 surrounds practically all of the extracerebral portion of the probe 11, and serves to keep its internal environment sterile. It is flexible and transparent so as to enable the clamping screws 23 and 29 to be operated and so as to enable the graduations present on the inner and outer parts 20 and 22 to be read.

There follows a description of a third example of a probe of the invention. This third probe example differs from that of FIG. 2 solely in the outer part of the probe, and consequently it is only this outer part 122 that is described.

Figure 3:
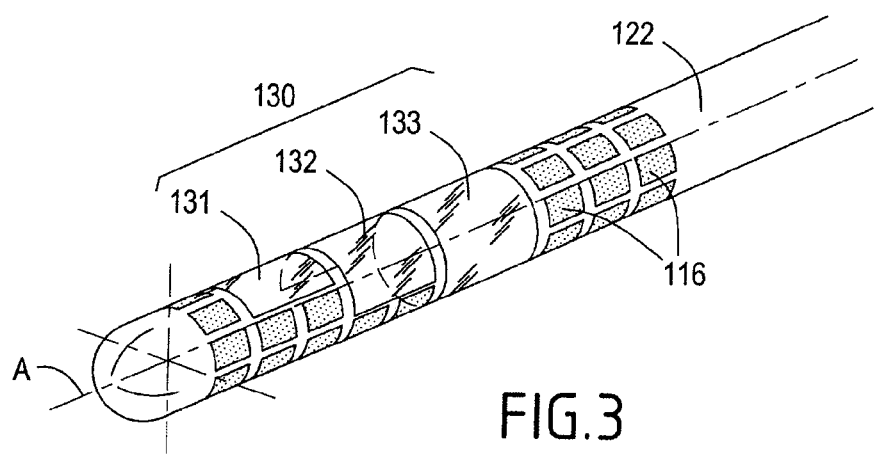
FIG. 3 is a perspective view of the outer part of a third example of a probe of the invention.

FIG. 3 is a perspective view of the outer part 122, and more precisely of the distal end portion of said outer part.

The outer part 122 is closed at its distal end and presents first, second, and third small lateral windows 131, 132, and 133 that are juxtaposed along the longitudinal axis A of the outer part 122, thereby providing a (large) lateral treatment window 130. The circumferential width of the window 130 varies along the axis A of the outer part 122 as follows: on going away from the distal end of the outer part 122, this circumferential width increases. More precisely, the first window 131 presents an aperture angle of 90° about the longitudinal axis A (its circumferential width thus corresponds to one-fourth of the circumference of the outer part 122); the second window 132 has an aperture angle of 180° about the longitudinal axis A (its circumferential width thus corresponds to half the circumference of the outer part 122); and the third window 133 has an aperture angle of 360° about the longitudinal axis A (its circumferential width thus corresponds to the circumference of the outer part 122). These three windows are in alignment such that their midplanes containing the axis A coincide.

This specific shape for the window 130 makes it possible to treat brain zones that are of complex shape, since by moving the treatment means (i.e. the first part of the probe) along the longitudinal axis A of the outer part 122, and by turning the outer part 122 about its axis A (where necessary), it is possible to perform treatment in a particular angular direction, and with an aperture angle (or therapy arc) that is complete at 360°, or partial at 90° or 180°.

The detectors 116, e.g. electrodes, are distributed axially and circumferentially around the axis A, and more particularly around the small windows 131, 132, and 133, both upstream and downstream therefrom.

When the probe has laser treatment means, said lateral treatment window 130 is a window that is transparent to the laser radiation emitted by the treatment means.

When the probe has cryogenic treatment means, said lateral treatment window 130 is a zone having thermal conductivity that is greater than that of the remainder of the outer part 122 (with the remainder of the outer part preferably being made of a material that is a good thermal insulator).

There follows a description of a treatment method using a probe of the invention.

In its most general form, this treatment method consists in:
identifying a brain dysfunction zone with the help of the detectors fitted to a probe of the invention;
moving the inner part of the probe so as to bring the treatment means up to the identified dysfunctional zone; and
activating the treatment means to treat this zone by laser or cryogenically.

In an implementation, the above-mentioned brain dysfunction zone is identified by detecting electrical activity in various zones of the brain by using the detection electrodes.

In an implementation, the probe is implanted by stereotaxy or by a robotic neuronavigation system under local or general anesthetic.

In an implementation, for the detection step, measurements are taken simultaneously in a plurality of adjacent zones situated in the same region of the brain, with the help of a probe of the invention carrying a plurality of detectors.

In an implementation, during treatment, information is recovered from the detectors situated in the zone being treated, and the operation of said treatment means is modulated as a function of the recovered information. Thus, the effectiveness of the treatment can be verified and it can be decided to increase or decrease the intensity of the treatment accordingly, or even to stop treatment if it is found that the originally detected dysfunction has disappeared.

In practice, the probe is not implanted at random in the brain. Particular regions of the brain in which neurological dysfunctions appear to arise, e.g. during an attack of epilepsy are previously identified by MRI. Thereafter, the implantation coordinates and trajectories for the probe are calculated by stereotaxy. To implant the probe, it is preferable to use a stereotaxic frame. The frame constitutes a guide outside the skull for trepanning the hole in the skull through which the probe is to pass. Alternatively, it is also possible to implant the probe using a robotic neuronavigation system. The probe is inserted into the brain until the portion carrying the detection electrodes reaches the previously identified zone. It is possible to track and measure the movement of the probe (or indeed the various portions thereof) by MRI.

When a guide 26 of the kind shown in FIG. 2 is used, the guide is screwed into the trepanned hole and the probe is passed through the guide.

Advantageously, for the diagnosis and position-identifying step, the signals detected by the detectors are analyzed in order to identify abnormal brain activity, representative of tissue dysfunction. Thereafter, knowledge of the position of the probe in the brain and of the positions on the probe of the detectors that have detected abnormal activity, it is possible to calculate the position of the dysfunctional zone in the frame of reference of the brain. It should be observed that to treat epilepsy, the probe can remain implanted in the same position for several hours or even several days before any such dysfunction is identified.

When a probe carrying a plurality of detectors is implanted in a stationary position, the accuracy with which position is identified depends on the distribution of the detectors (i.e. on their spacing). In addition, the closer the detectors are to one another, the more numerous they must be in order to cover a region of the brain that is sufficiently large.

For the probe movement step, it is possible to use robotic actuator means or to perform these movements manually. Under such circumstances, it is preferable for the probe to carry graduations that enable its position to be identified.

An example of the system of the invention enabling a treatment method of the above-described type to be performed is shown diagrammatically in FIG. 4. The system comprises a probe 1, 11 of the invention of the type shown in FIG. 1 or 2, and a signal analyzer unit 50 connected to the detectors 6, 16 of the probes 1, 11 by the electric wires 7, 17. In the example, a multiplexer 51 is provided between the wires 7, 17 and the unit 50. The signal analyzer unit 50 receives, for example, a signal of the EEG type coming from each pair of detectors. It processes this signal so as to identify therein any anomalies representative of tissue dysfunction. Once an anomaly has been detected, it transmits information to the calculation and control unit 52 to which it is connected, informing it that an anomaly has been detected by one or more such detectors. The calculation and control unit 52 can then calculate the position in the brain of the dysfunction brain zone.

The unit 52 can then either communicate the determined position to the surgeon so as to move the destruction means manually, or else it can control actuator means 54, if any, that are suitable for moving the probe 1 or the inner part 22 of the probe 11 in order to bring the destruction means to the identified dysfunctional zone.

Once the destruction means are in place, the surgeon or the calculation and control unit 52 activates the destruction means.

For example, the calculation and control unit 52 switches on the laser 56 which generates laser radiation.

The calculation and control unit continues to receive via the signal analyzer unit 50 information that comes from the detectors 6, 16 that are situated in the treatment zone. As a function of this information, the calculation and control unit modulates the intensity of the treatment.

The calculation and control unit 52 is also connected to an MRI appliance 58 that enables the movement of the probe inside the brain to be tracked prior to treatment and that enables proper positioning to be verified, and that also serves to verify the intensity and the dissipation of heat within the brain while treatment is taking place. In the event of excessive heating that might constitute a danger for the patient, the unit 52 can issue an alarm signal for the attention of the surgeon or can itself deactivate the destruction means (e.g. by switching off the laser 56). MRI tracking also makes it possible to verify the effectiveness of the treatment that has been performed, thereby enabling the intensity of the treatment to be modulated.

Preferably, all of the materials constituting the probe 1, 11 are selected to be compatible with MRI so as to make such MRI monitoring possible.

The invention claimed is:

1. An intracerebral probe comprising: a first part with laser treatment means, and further comprising: a hollow second part surrounding the first part and having a longitudinal axis, the first part sliding inside the second part along said longitudinal axis; a plurality of detectors carried by the second part and distributed along a portion of the second part for identifying a brain dysfunction zone along the longitudinal axis of the second part; and a cooling system provided in the first part of the probe; wherein the laser treatment means is configured to treat the dysfunction zone by heating the dysfunction zone and the cooling system is configured to limit the heating.

2. An intracerebral probe according to claim 1, in which the detectors are electrodes, each electrode being adapted for detecting electrical activity in a zone of the brain surrounding the electrodes.

3. An intracerebral probe according to claim 1, in which the detectors are distributed circumferentially over the second part, around the longitudinal axis of the second part, or are segmented circumferentially so as to identify a position of the brain dysfunction zone angularly around said longitudinal axis.

4. An intracerebral probe according to claim 1, in which the second part of the probe presents a lateral treatment window enabling an action of the laser treatment means to be directed, said lateral treatment window being a window that is transparent to laser radiation emitted by said laser treatment means.

5. An intracerebral probe according to claim 4, in which said lateral treatment window extends along the longitudinal axis of the second part and/or circumferentially around said longitudinal axis of the second part.

6. An intracerebral probe according to claim 5, in which a circumferential width of said lateral treatment window varies along the longitudinal axis of the second part.

7. An intracerebral probe according to claim 1, including a fastener system mounted on one or the other of the first and second parts of the probe and adapted to hold the first and second parts of the probe fixed in a determined relative position.

8. An intracerebral probe according to claim 1, such that all of the materials constituting the intracerebral probe are compatible with MRI, thereby making it possible to perform MRI monitoring while using the intracerebral probe.

9. A kit comprising the intracerebral probe according to claim 1, a guide for guiding the second part of the probe while it is being implanted in the brain, and a fastener system for holding said second part and the guide fixed in a determined relative position.

10. A kit according to claim 9, comprising a plastic sheath extending between said guide and an extracranial end of the first part of the probe so as to maintain a sterile environment for junctions between the guide and the second part of the probe, and between the first and second parts of the probe.

11. A treatment system comprising the intracerebral probe according to claim 1 and a control system for controlling operation of said laser treatment means, said control means system being connected to the detectors of the probe and adapted for, during treatment, receiving information from said detectors and modulating the operation of said laser treatment means as a function of the information received.

12. A treatment system according to claim 11, further comprising a connection system for connecting said control system to an MRI appliance so as to, during treatment, receive information from said MRI appliance and modulate the operation of said laser treatment means as a function of the information received.

13. A treatment system according to claim 11, including a position-identifier system co-operating with said detectors of the probe in order to identify a position of the brain dysfunction zone, and actuator(s) for moving the first part of the probe in such a manner as to bring the laser treatment means up to the identified position of the brain dysfunction zone.

14. An intracerebral probe according to claim 1, wherein said cooling system is a system for moving cooling liquid back and forth.

15. A treatment method comprising the following steps:
identifying the brain dysfunction zone, based on information collected by the detectors of the intracerebral probe of claim 1;
moving the first part of the intracerebral probe so as to bring the laser treatment means up to the dysfunction zone.

16. The treatment method of claim 15, wherein the information collected by the detectors is a brain electrical activity.

17. The treatment method of claim 15, wherein the intensity of the heating treatment is modulated based on information collected by the detectors during treatment.

18. The treatment method of claim 15, wherein the intensity of the heating treatment is modulated based on heating information collected by MRI during treatment.

19. The treatment method of claim 15, wherein moving and positioning of the intracerebral probe are tracked by MRI.

20. The treatment method of claim 15 used for treating epilepsy.

21. An intracerebral probe according to claim 1, wherein the second part of the probe has first, second, and third lateral windows juxtaposed along the longitudinal axis of the second part, the first lateral window having an aperture angle of 90 degrees about the longitudinal axis, the second lateral window having an aperture angle of 180 degrees about the longitudinal axis, and the third lateral window having an aperture angle of 360 degrees about the longitudinal axis.

* * * * *